US00PP19183P2

(12) United States Plant Patent
Verschoor

(10) Patent No.: US PP19,183 P2
(45) Date of Patent: Sep. 9, 2008

(54) ***PHLOX* PLANT NAMED 'GRENADINE DREAM'**

(50) Latin Name: *Phlox paniculata*
Varietal Denomination: Grenadine Dream

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 4 days.

(21) Appl. No.: 11/725,797

(22) Filed: Mar. 20, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
(74) *Attorney, Agent, or Firm*—C. A. Whealy

(57) ABSTRACT

A new and distinct cultivar of *Phlox* plant named 'Grenadine Dream', characterized by its upright and relatively compact plant habit; freely flowering habit; red purple-colored flowers; relative resistance to Powdery Mildew; and good garden performance.

2 Drawing Sheets

Botanical designation: *Phlox paniculata.*
Cultivar denomination: 'Grenadine Dream'.

BACKGROUND OF THE INVENTION

The present invention relates to a new and distinct cultivar of *Phlox,* botanically known as *Phlox paniculata* and hereinafter referred to by the name 'Grenadine Dream'.

The new *Phlox* is a product of a planned breeding program conducted by the Inventor in Haarlem, The Netherlands. The objective of the breeding program was to create new compact *Phlox* cultivars with attractive flower coloration and Powdery Mildew resistance.

The new *Phlox* originated from a cross-pollination made by the Inventor in 2004 in Haarlem, The Netherlands, of two unidentified selections of *Phlox paniculata,* not patented. The new *Phlox* was discovered and selected by the Inventor as a single flowering plant within the progeny of the stated cross-pollination in a controlled environment in Haarlem, The Netherlands in 2005.

Asexual reproduction of the new *Phlox* by cuttings in a controlled environment in Haarlem, The Netherlands since 2005, has shown that the unique features of this new *Phlox* are stable and reproduced true to type in successive generations.

SUMMARY OF THE INVENTION

The cultivar Grenadine Dream has not been observed under all possible environmental conditions. The phenotype may vary somewhat with variations in environment and cultivar practices such as temperature and light intensity without, however, any variance in genotype.

The following traits have been repeatedly observed and are determined to be the unique characteristics of 'Grenadine Dream'. These characteristics in combination distinguish 'Grenadine Dream' as a new and distinct cultivar of *Phlox:*

1. Upright and relatively compact plant habit.
2. Freely flowering habit.
3. Red purple-colored flowers.

4. Relatively resistant to Powdery Mildew.
5. Good garden performance.

Plants of the new *Phlox* and the parent selections differ primarily in flower coloration and plant height.

Plants of the new *Phlox* can be compared to plants of the cultivar Red Riding Hood, not patented. In side-by-side comparisons conducted in Haarlem, The Netherlands, plants of the new *Phlox* and the cultivar Red Riding Hood differed in the following characteristics:

1. Plants of the new *Phlox* were more compact than plants of the cultivar Red Riding Hood.
2. Plants of the new *Phlox* wee sturdier and had thicker stems than plants of the cultivar Red Riding Hood.
3. Plants of the new *Phlox* had darker green-colored and healthier leaves than plants of the cultivar Red Riding Hood.
4. Plants of the new *Phlox* had darker-colored flowers than plants of the cultivar Red Riding Hood.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph on the first sheet comprises a side perspective view of a typical flowering plant of 'Grenadine Dream' grown in a container.

The photograph at the top of the second sheet is a close-up view of a typical inflorescence of 'Grenadine Dream'.

The photograph at the bottom of the second sheet is a close-up view of the upper surface of a typical leaf of 'Grenadine Dream'.

DETAILED BOTANICAL DESCRIPTION

The aforementioned photographs and following observations, measurements and values describe plants grown in Haarlem, The Netherlands, under commercial practice during the early autumn in an outdoor nursery with day temperatures ranging from 14° C. to 32° C. and night temperatures ranging from 5° C. to 15° C. Plants were grown for about one year when the photographs and description were taken. In the following description, color references are made to The Royal Horticultural Society Colour Chart, 2001 Edition, except where general terms of ordinary dictionary significance are used.

Botanical classification: *Phlox paniculata* cultivar Grenadine Dream.

Parentage:

*Female, or seed, parent.*—Unidentified selection of *Phlox paniculata,* not patented.

*Male, or pollen, parent.*—Unidentified selection of *Phlox paniculata,* not patented.

Propagation:

*Type.*—By cuttings.

*Time to produce a rooted plant.*—About one month during the spring in The Netherlands.

*Root description.*—Fine; white in color.

Plant description:

*Plant form/habit.*—Upright and relatively compact plant habit; narrow inverted triangle; low to moderately vigorous growth habit.

*Plant height.*—About 33.8 cm.

*Plant width* (*spread*).—About 20.2 cm.

*Lateral branches.*—Length: About 16.6 cm. Diameter: About 4 mm. Internode length: About 1.9 cm. Strength: Strong. Texture: Smooth, glabrous. Color: 144B.

Foliage description:

*Arrangement.*—Opposite, simple.

*Length.*—About 9.7 cm.

*Width.*—About 3.2 cm.

*Shape.*—Elliptic.

*Apex.*—Apiculate.

*Base.*—Truncate to obtuse.

*Margin.*—Finely serrate.

*Texture, upper and lower surfaces.*—Smooth, glabrous.

*Venation pattern.*—Pinnate.

*Color.*—Developing leaves, upper surface: 143A. Developing leaves, lower surface: Between 143C and 144B. Fully expanded leaves, upper surface: 137A; venation, 145A. Fully expanded leaves, lower surface: 138B; venation, 146D.

*Petiole.*—Length: About 3 mm. Diameter: About 4 mm. Texture, upper and lower surfaces: Smooth, glabrous. Color, upper and lower surfaces: 145A to 145B.

Flower description:

*Flower type/habit.*—Single rotate and salverform flowers arranged in compound terminal panicles; flowers face upright and outward. Panicles roughly conical in shape. Freely flowering habit with about 175 flower buds and flowers developing per inflorescence.

*Fragrance.*—Moderately fragrant; sweet.

*Natural flowering season.*—Continuously flowering from July until September in Haarlem, The Netherlands. Flowers not persistent.

*Postproduction longevity.*—Flowers last about ten days on the plant and about ten days as a cut flower.

*Flower buds.*—Height: About 1.3 cm. Diameter: About 5 mm. Shape: Elliptic. Color: 64A to 64C; towards the base, 65C to 65D; calyx, 145A flushed with 187A.

*Inflorescence height.*—About 17.2 cm.

*Inflorescence diameter.*—About 12.5 cm.

*Flower diameter.*—About 2.9 cm.

*Flower depth.*—About 2.7 cm.

*Petals.*—Quantity per flower: Typically five in a single whorl; petals fused at the base into a narrow tube. Length: About 3.6 cm. Lobe width: About 1.8 cm. Shape: Spatulate. Apex: Obtuse. Margin: Entire. Texture, upper and lower surfaces: Smooth, glabrous. Color: Developing petals, upper surface: N57A to N57B; towards the throat, 60B; throat, 64D. Developing petals, lower surface: 64C to 64D; tube, 59C to 59D. Fully expanded petals, upper surface: Between N57A and N66A; towards the throat, 60B; throat, N77B. Color becoming closer to N57B with development. Fully expanded petals, lower surface: 63A to 63C; tube, N77B.

*Sepals.*—Quantity per flower: Typically five in a single whorl, fused towards the base; companulate calyx. Length: About 9 mm. Width: About 1.7 mm. Shape: Lanceolate. Apex: Narrowly apiculate. Margin: Entire. Texture, upper and lower surfaces: Smooth, glabrous. Color, developing sepals, upper and lower surfaces: 145A flushed with 187A. Color, fully expanded sepals, upper surface: N186C. Color, fully expanded sepals, lower surface: 144C to 144D.

*Peduncles.*—Length: About 13.8 cm. Diameter: About 3 mm. Angle: Main peduncle, erect; lateral peduncles, about 40° from vertical. Strength: Strong. Texture: Smooth, glabrous. Color: 144B to 144C.

*Pedicels.*—Length: About 5 mm. Diameter: About 1 mm. Angle: Erect to about 60° from vertical. Strength: Strong. Texture: Smooth, glabrous. Color: 146A.

*Reproductive organs.*—Stamens: Quantity per flower: Typically five; fused with petals in tube. Filament length: About 1 mm. Anther shape: Oblong. Anther length: About 2 mm. Anther color: 155A. Pollen amount: Scarce. Pollen color: 158D. Pistils: Quantity per flower: One. Pistil length: About 1.8 cm. Stigma shape: Three-parted. Stigma color: 150C to 150D. Style length: About 1.7 cm. Style color: 183C. Ovary color: 143A.

*Seed/fruit.*—Seed and fruit development have not been observed.

Disease/pest resistance: Plants of the new *Phlox* have been noted to be relatively resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and temperatures ranging from about −10° C. to about 35° C.

It is claimed:

1. A new and distinct *Phlox* plant named 'Grenadine Dream' as illustrated and described.

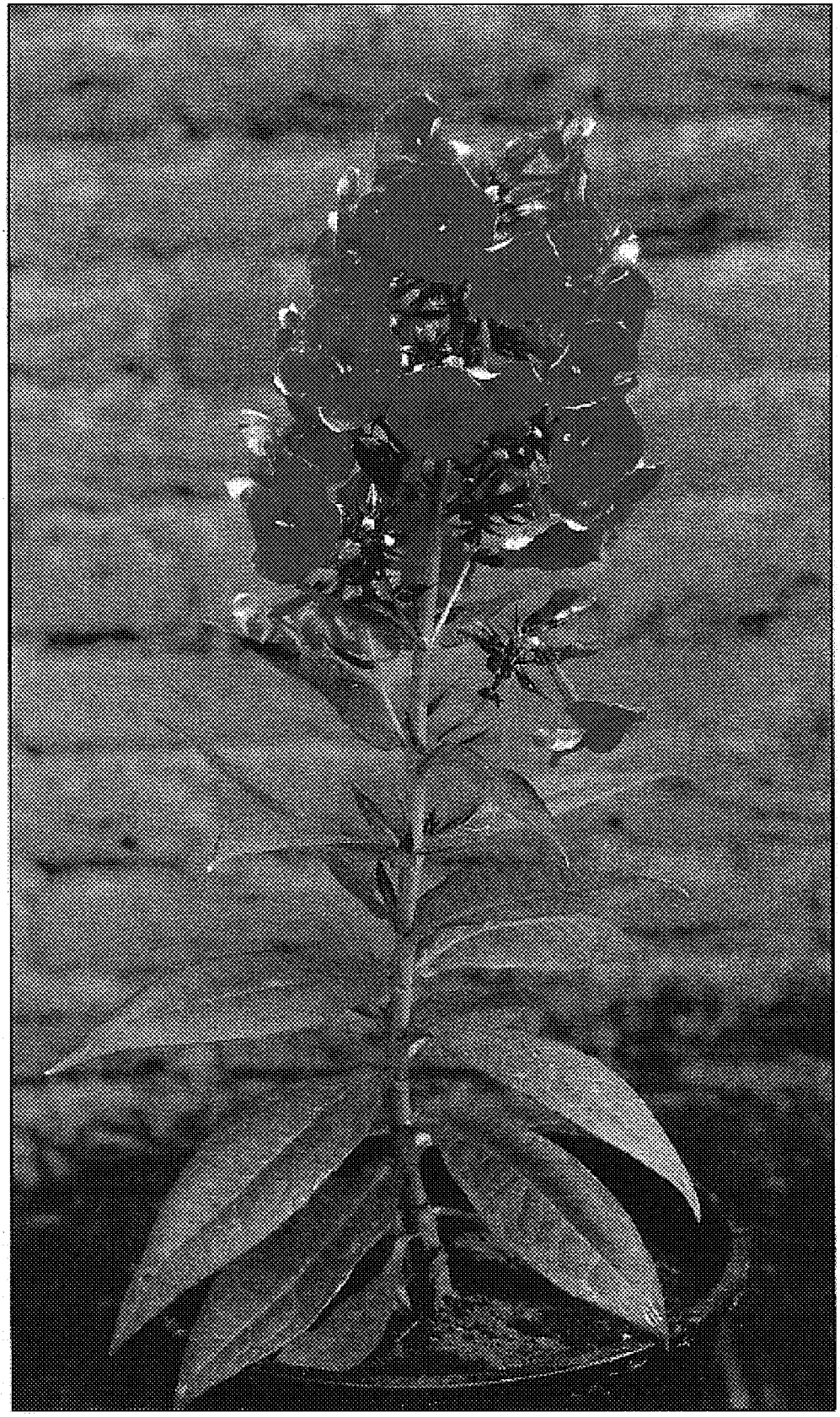

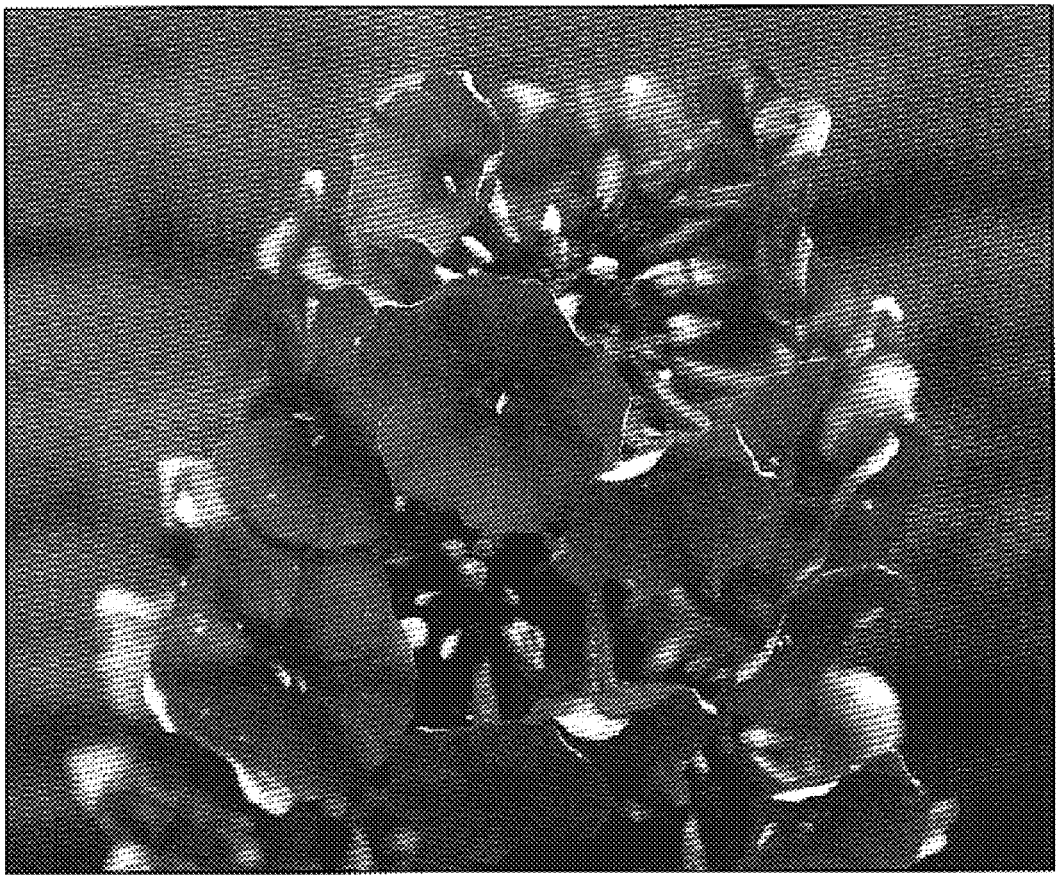
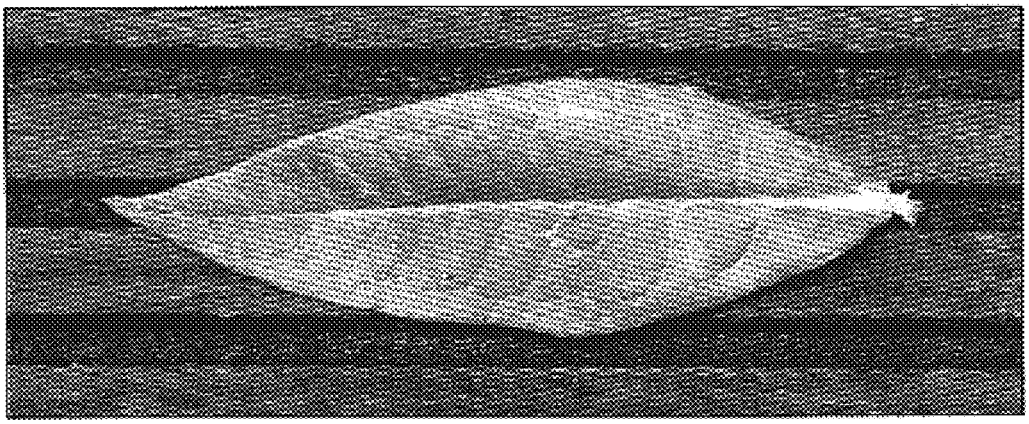

* * * * *